United States Patent
Schilling et al.

(10) Patent No.: US 7,864,918 B2
(45) Date of Patent: *Jan. 4, 2011

(54) X-RAY MACHINE FOR BREAST EXAMINATION HAVING A GANTRY INCORPORATED IN A PATIENT TABLE

(75) Inventors: Harry Schilling, Eichstaett (DE); Willi Kalender, Moehrendorf (DE)

(73) Assignee: MIR Medical Imaging Research Holding GmbH, Moehrendorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/401,765

(22) Filed: Mar. 11, 2009

(65) Prior Publication Data

US 2010/0080344 A1    Apr. 1, 2010

(30) Foreign Application Priority Data

Sep. 29, 2008  (DE) ................... 10 2008 042 430

(51) Int. Cl.
*A61B 6/04* (2006.01)
(52) U.S. Cl. ........................ 378/37; 378/196
(58) Field of Classification Search ............ 378/37, 378/195–198, 209, 208
See application file for complete search history.

(56) References Cited

U.S. PATENT DOCUMENTS

| | | |
|---|---|---|
| 3,673,394 A | 6/1972 | Hartmann |
| 4,015,836 A | 4/1977 | Redington et al. |
| 4,400,827 A | 8/1983 | Spears |
| 4,680,028 A | 7/1987 | Stuart |
| 4,709,382 A | 11/1987 | Sones |
| 5,273,435 A | 12/1993 | Jacobson |
| 5,308,321 A | 5/1994 | Castro |
| 5,386,447 A | 1/1995 | Siczek |
| 5,426,685 A | 6/1995 | Pellegrino et al. |
| 5,528,043 A | 6/1996 | Spivey et al. |
| 5,569,266 A | 10/1996 | Siczek |
| 5,609,827 A | 3/1997 | Russell et al. |

(Continued)

FOREIGN PATENT DOCUMENTS

DE    19639975    5/1998

(Continued)

OTHER PUBLICATIONS

Mun et al., "Active RFID System Augmented with 2D Barcode for Asset Management in a Hospital Setting," IEEE International Conference on RFID, Mar. 2007, pp. 205-211.

(Continued)

*Primary Examiner*—Hoon Song
(74) *Attorney, Agent, or Firm*—Kevin L. Daffer; Daffer McDaniel, LLP

(57) ABSTRACT

An X-ray machine for imaging a breast of a female patient comprises a gantry with an X-ray tube and an X-ray detector, and a horizontally disposed patient table with a cut-out portion for accommodating a breast of the patient. The gantry is rigidly mechanically suspended from the patient table. The gantry is adapted to rotate about an approximately vertical rotational axis in continuous rotational movement for imaging the breast. The gantry is also adapted to be moved in a vertical direction during said the rotational movement.

6 Claims, 3 Drawing Sheets

U.S. PATENT DOCUMENTS

| | | | |
|---|---|---|---|
| 5,664,569 | A | 9/1997 | Damadian et al. |
| 5,757,878 | A | 5/1998 | Dobbs et al. |
| 5,803,912 | A | 9/1998 | Siczek et al. |
| 6,242,743 | B1 | 6/2001 | DeVito et al. |
| 6,254,614 | B1 | 7/2001 | Jesseph |
| 6,298,114 | B1 | 10/2001 | Yoda |
| 6,325,537 | B1 | 12/2001 | Watanabe |
| 6,358,246 | B1 | 3/2002 | Behl et al. |
| 6,415,012 | B1 | 7/2002 | Taguchi et al. |
| 6,418,188 | B1 | 7/2002 | Broadnax |
| 6,419,390 | B1 | 7/2002 | Landis-Lowell |
| 6,463,122 | B1* | 10/2002 | Moore ................ 378/65 |
| 6,480,565 | B1 | 11/2002 | Ning |
| 6,684,097 | B1 | 1/2004 | Parel et al. |
| 6,819,736 | B1 | 11/2004 | Bruder et al. |
| 6,837,772 | B1 | 1/2005 | Luk |
| 6,872,001 | B1 | 3/2005 | Gilevich |
| 7,005,988 | B2 | 2/2006 | Mathewson, II et al. |
| 7,065,393 | B2 | 6/2006 | Sati et al. |
| 7,304,578 | B1 | 12/2007 | Sayers et al. |
| 7,453,978 | B1 | 11/2008 | DiBianca et al. |
| 7,467,892 | B2 | 12/2008 | Lang et al. |
| 7,492,858 | B2 | 2/2009 | Partain et al. |
| 7,556,426 | B2 | 7/2009 | Nakajo et al. |
| 7,558,370 | B2 | 7/2009 | Sommer, Jr. et al. |
| 7,677,799 | B2 | 3/2010 | Jensen et al. |
| 7,697,660 | B2 | 4/2010 | Ning |
| 7,743,953 | B2 | 6/2010 | Okazaki et al. |
| 7,764,765 | B2 | 7/2010 | Ohta et al. |
| 2002/0181651 | A1 | 12/2002 | Shepherd et al. |
| 2003/0072409 | A1 | 4/2003 | Kaufhold et al. |
| 2003/0204965 | A1 | 11/2003 | Hennessey |
| 2004/0066880 | A1 | 4/2004 | Oikawa |
| 2004/0082856 | A1 | 4/2004 | Marmarelis |
| 2004/0092826 | A1 | 5/2004 | Corbeil et al. |
| 2004/0238750 | A1 | 12/2004 | Vafi et al. |
| 2004/0251419 | A1 | 12/2004 | Nelson et al. |
| 2004/0254461 | A1 | 12/2004 | Ackerman, III |
| 2005/0070817 | A1 | 3/2005 | Mueller, Jr. |
| 2006/0094950 | A1* | 5/2006 | Ning ................ 600/407 |
| 2006/0145871 | A1 | 7/2006 | Donati et al. |
| 2006/0262898 | A1 | 11/2006 | Partain et al. |
| 2007/0009080 | A1 | 1/2007 | Mistretta |
| 2007/0064867 | A1 | 3/2007 | Hansen et al. |
| 2007/0092059 | A1 | 4/2007 | Eberhard et al. |
| 2007/0237306 | A1* | 10/2007 | Jones et al. ................ 378/195 |
| 2007/0238957 | A1 | 10/2007 | Yared |
| 2008/0033420 | A1 | 2/2008 | Nields et al. |
| 2008/0037703 | A1 | 2/2008 | Ting |
| 2008/0081984 | A1 | 4/2008 | Lafferty |
| 2008/0084961 | A1 | 4/2008 | Keppel et al. |
| 2008/0089471 | A1* | 4/2008 | Kobayashi ................ 378/37 |
| 2008/0101538 | A1 | 5/2008 | Schliermann |
| 2008/0187095 | A1 | 8/2008 | Boone et al. |
| 2008/0205588 | A1 | 8/2008 | Kim |
| 2008/0221443 | A1 | 9/2008 | Ritchie et al. |
| 2008/0221478 | A1 | 9/2008 | Ritchie et al. |
| 2008/0230074 | A1 | 9/2008 | Zheng et al. |
| 2009/0080604 | A1 | 3/2009 | Shores et al. |
| 2009/0196393 | A1 | 8/2009 | Wang et al. |

FOREIGN PATENT DOCUMENTS

| | | |
|---|---|---|
| DE | 19812995 | 10/1999 |
| DE | 10026792 | 12/2001 |
| DE | 10207623 | 11/2003 |
| DE | 102004042790 | 3/2006 |
| DE | 102005022347 | 11/2006 |
| DE | 102005048049 | 4/2007 |
| EP | 0435837 | 7/1991 |
| EP | 1549115 | 6/2005 |
| EP | 1700568 | 9/2006 |
| EP | 1864611 | 12/2007 |
| JP | 2008272093 | 11/2008 |
| WO | 93/17620 | 9/1993 |
| WO | 94/06352 | 3/1994 |
| WO | 98/49939 | 11/1998 |
| WO | 99/30615 | 6/1999 |
| WO | 2004/006755 | 1/2004 |
| WO | 2004/043535 | 5/2004 |
| WO | 2006/119426 | 11/2006 |
| WO | 2007/120622 | 10/2007 |
| WO | 2008/024611 | 2/2008 |
| WO | 2008/054279 | 5/2008 |

OTHER PUBLICATIONS

Nishide et al., "Micro-focus x-ray CT imaging of breast specimens with microcalcifications," 89th Scientific Assembly and Annual Meeting of the Radiological Society of North America, Dec. 2003, pp. 1662-1663.

Tornai et al., "Design and Development of a Fully-3D Dedicated X-ray Computed Mammotomography System," Proceedings of SPIE, vol. 5745, 2005, pp. 189-197.

Bentzen et al., "Isotherm mapping in hyperthermia using subtraction X-ray computed tomography," Radiotherapy and Oncology, vol. 2, 1984, pp. 255-260.

Griffiths et al., "Applied potential tomography for non-invasive temperature mapping in hyperthermia," Clin. Phys. Physiol. Meas., vol. 8, Suppl. A, 1987, pp. 147-153.

Jenne et al, "CT On-Line Monitoring of HIFU Therapy," IEEE Ultrasonics Symposium, 1997, pp. 1377-1380.

Fallone et al., "Noninvasive thermometry with a clinical x-ray CT scanner," Med. Phys., vol. 9, No. 5, 1982, pp. 715-721.

Office Action mailed Apr. 14, 2010 for U.S. Appl. No. 12/402,059.
Office Action mailed Apr. 1, 2010 for U.S. Appl. No. 12/402,141.
Office Action mailed Jun. 16, 2010 for U.S. Appl. No. 12/401,906.
Office Action mailed Jun. 10, 2010 for U.S. Appl. No. 12/401,735.
Office Action mailed Jul. 13, 2010 for U.S. Appl. No. 12/402,225.
Office Action mailed May 11, 2010 for U.S. Appl. No. 12/401,814.
Office Action mailed Sep. 23, 2010 for U.S. Appl. No. 12/401,792.
Notice of Allowance mailed Sep. 17, 2010 for U.S. Appl. No. 12/402,059.

* cited by examiner

X-RAY MACHINE FOR BREAST EXAMINATION HAVING A GANTRY INCORPORATED IN A PATIENT TABLE

PRIORITY CLAIM

This application claims priority to pending German Application No. DE102008042430.7 filed on Sep. 29, 2008.

BACKGROUND OF THE INVENTION

1. Field of the Invention

The invention relates to an X-ray machine for imaging a female breast (mammography).

2. Description of Related Art

Various X-ray machines are known for performing an examination of a female breast. In these X-ray machines, a rotating gantry having an X-ray tube and an X-ray detector is located below a patient table on which a female patient rests. A machine of this kind is described in U.S. Pat. No. 4,015,836. Disadvantages of the X-ray machine described in the '836 patent include a large space requirement and the lack of accessibility to the breast being examined. Furthermore, the patient is put into a relatively uncomfortable posture with her head in a low position to maximize the amount of breast accessible to the X-ray device.

An improvement to the aforementioned device is provided in U.S. Publication No. 2006/0094950. The patient is afforded a more comfortable position in the X-ray machine disclosed in the '950 publication. However, the breast to be examined is accessible only with special instruments. In addition, the X-ray machine disclosed in the '950 publication requires a large amount of space, due to the large constructional size of the gantry.

U.S. Publication No. 2007/0064867 discloses an X-ray machine that is based on a spiral computer tomography (CT) scanner. Although the X-ray machine described in the '867 publication requires less space, resolution is limited in this machine by a mechanical design which provides low stability. Another disadvantage of this machine is that the breast is not accessible from the outside of the machine.

BRIEF SUMMARY OF THE INVENTION

The following description of the objective of the disclosure provided herein and the description of an embodiment of an X-ray machine for imaging a breast is not to be construed in any way as limiting the subject matter of the appended claims.

The objective of the disclosure provided herein is to design an X-ray machine for imaging a female breast in a diagnostically correct manner, rapidly, at low cost, and in a comfortable position for the patient.

An embodiment of an X-ray machine for imaging a breast of a female patient includes an approximately horizontally disposed patient table with a cut-out portion for accommodating a breast of a female patient, and a gantry rigidly suspended mechanically from the patient table. A gantry in accordance with this disclosure comprises an X-ray tube and the X-ray detector. The gantry is adapted to rotate about an approximately vertical rotational axis. The gantry is further adapted to be set into continuous rotational movement for imaging a breast. During said rotational movement, the gantry is further adapted to be moved in a vertical direction (e.g., by means of a gantry lift drive), with the vertical movement being dependent on the rotational movement.

BRIEF DESCRIPTION OF THE DRAWINGS

In the following, the invention will be described by way of example, without limitation of the general inventive concept, on examples of embodiment and with reference to the drawings.

Figure 1:
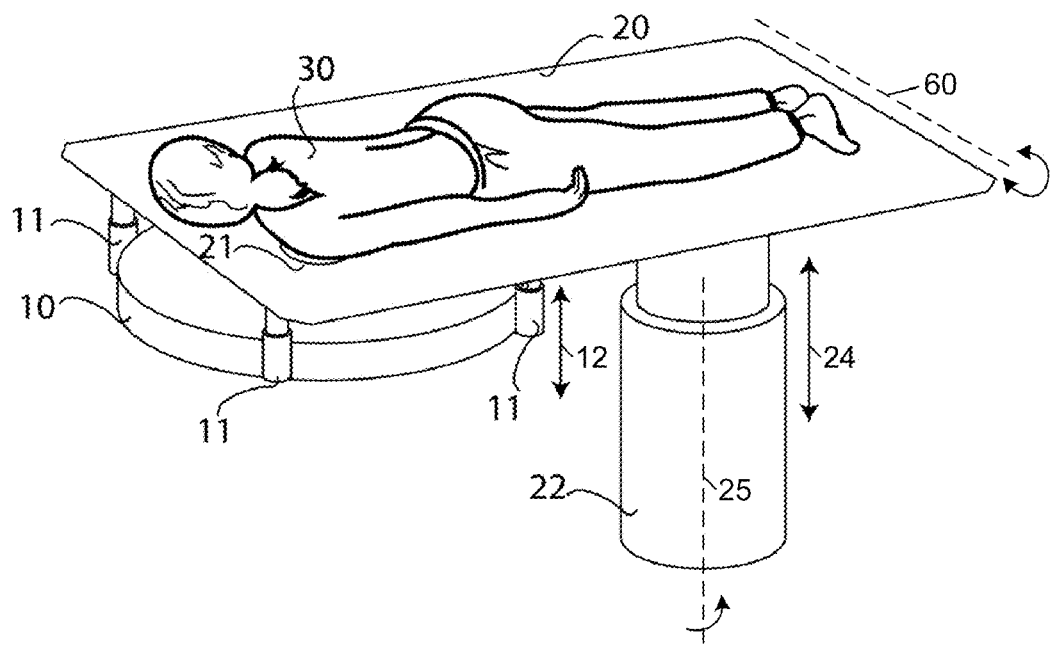
FIG. 1 shows a planar view of an X-ray machine having an adjustable height patient table, which is firmly installed.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

FIG. 1 illustrates an embodiment of an X-ray machine. A female patient 30 rests on a patient table 20. A breast to be examined is suspended through a breast cutout portion 21 in the surface of the patient table, so that the breast is within an exposure range of a gantry 10. In the illustrated embodiment, gantry 10 is a spiral computer tomograph (CT) gantry with an X-ray tube and an X-ray detector, which rotate around a breast to be examined. The breast is imaged during the rotation. Simultaneously with the rotation, a displacement in the vertical direction (denoted by arrow 12) is effected by a gantry lift drive 11, so that the breast is scanned along a spiraling direction. The height of the patient table 20 is adjustable (along arrow 24) with a patient table lift drive 22. If the patient table 20 is firmly installed, as shown in FIG. 1, it can be optionally rotated about an axis 25 of the patient table lift drive 22.

Figure 2:
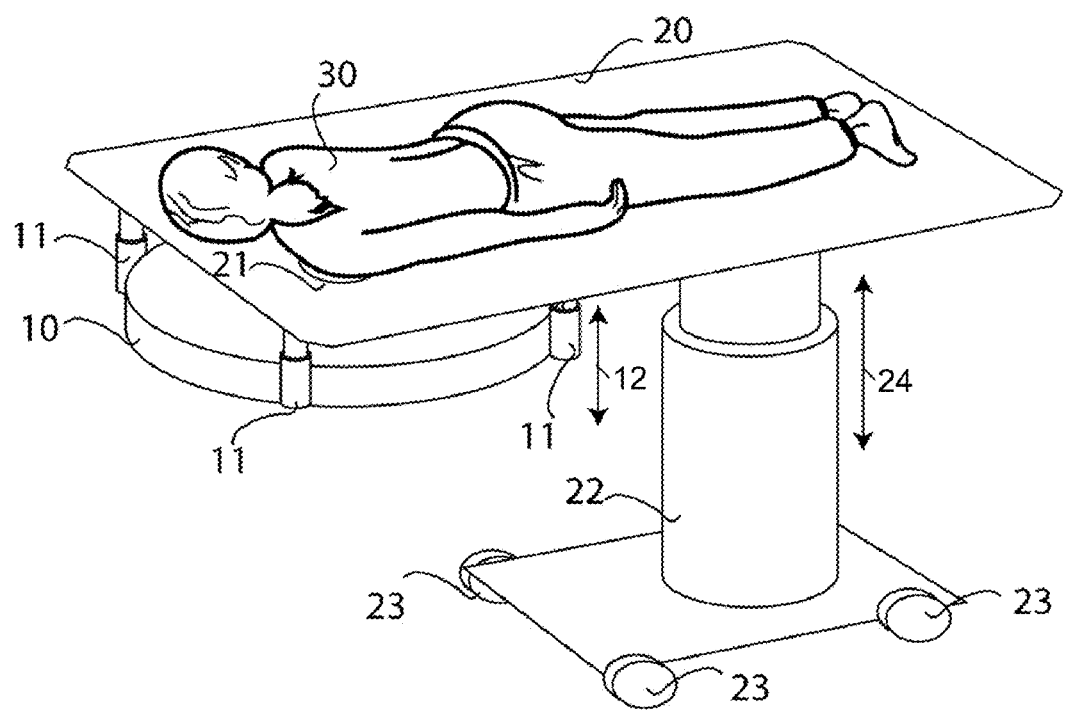
FIG. 2 shows a planar view of an X-ray machine having a movable patient table.

FIG. 2 illustrates another embodiment of an X-ray machine. The embodiment shown in FIG. 2 includes many of the components shown in FIG. 1 and described above. Components with like numerals will not be described herein for the sake of brevity. In addition to the components described above, the embodiment shown in FIG. 2 is provided with wheels 23 so that it may be moved in a simple manner.

Figure 3:
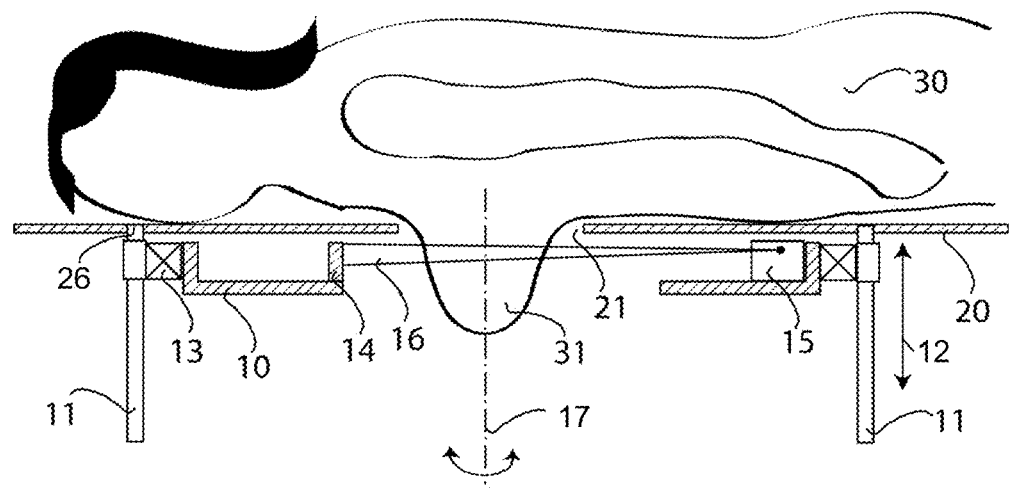
FIG. 3 shows a partial cross-sectional view through either one of the X-ray machines shown in FIG. 1 or 2.

FIG. 3 illustrates a partial cross-sectional view, which may be taken through either of the X-ray machines shown in FIG. 1 or 2. A female patient 30 is supported on the patient table 20 so that her breast 31 is suspended through a breast cutout portion 21 into an exposure range of a gantry 10. The gantry 10 is a spiral computer tomograph (CT) gantry with an X-ray tube 15 and an X-ray detector 14. The X-ray tube 15 and X-ray detector 14 are supported by a gantry pivot bearing 13, which allows the gantry 10 to be rotated about a rotational axis 17. Simultaneously with the rotation, a displacement in the vertical direction is effected by a gantry lift drive 11, so that the breast 31 is scanned along a spiraling direction. The gantry lift drive 11 is rigidly mechanically connected to the patient table 20 via a gantry suspension means 26.

Figure 4:
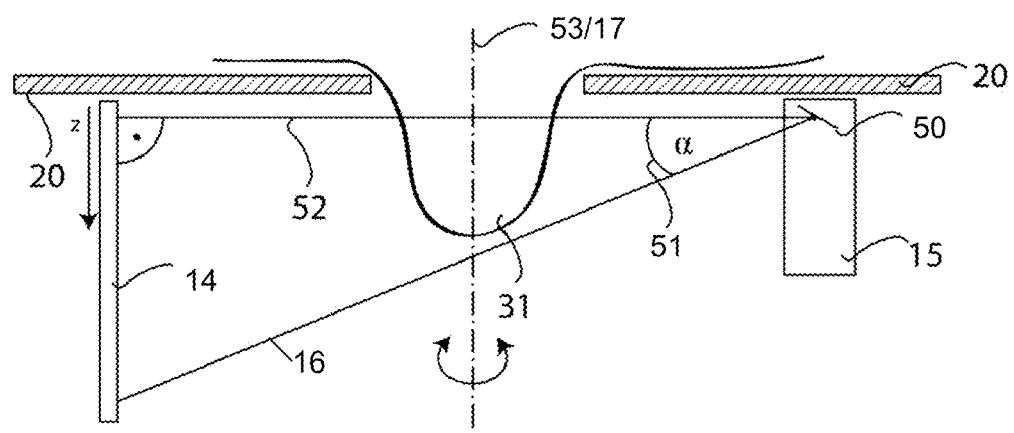
FIG. 4 shows a portion of the cross-sectional view shown in FIG. 3 to illustrate a beam path between the X-ray tube and X-ray detector of the X-ray machine.

FIG. 4 shows a magnified view of the cross-section provided in FIG. 3 to illustrate a path 16 of a beam of rays. As noted above, a patient's breast 31 is suspended through an opening 21 in a surface of a rest, which in this embodiment is designed to be a patient table 20. Of course, such an arrangement could be rotated through a range of desired angles 60 (FIG. 1), resulting in an alternative arrangement in which the patient table 20 is rotated around axis 60 (FIG. 1) so that the table 20 is inclined or stood upright. In such an alternative embodiment, the inclined or upright patient table may serve only as an abutment surface through which a breast can be inserted. In all embodiments, however, the wall of a patient's chest should rest as closely as possible against the patient table 20, so that the breast can be imaged as completely as possible.

To obtain images of the breast, gantry 10 rotates about the rotational axis 17, as shown in FIGS. 3 and 4. The X-ray tube 15 generates a beam of rays 16 which penetrates the breast 31 and is received by the detector 14. The beam is ideally limited to impinging only on an active face of the detector. It is generally not desired that the beam penetrate the patient table 20.

As best shown in FIG. 4, the beam generated by anode 50 within the X-ray tube 15 and extends toward the detector 14 with a cone angle $\alpha$ (51). A central ray 52, which is incident on the active face of the detector 14, is located at the top edge of the beam of rays 16 close to the patient table 20. A central axis 53 extending perpendicular to the central ray 52 is aligned, in the illustrated embodiment, with the rotational axis 17 of the gantry 10.

Figure 5:
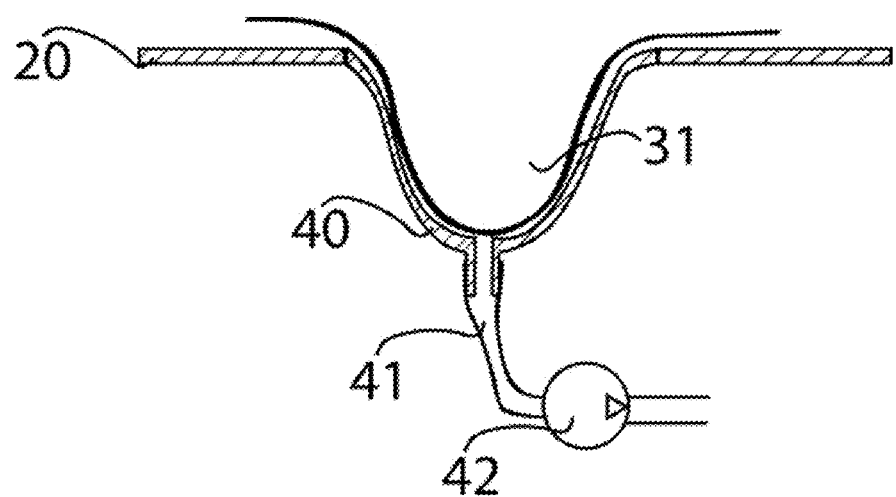
FIG. 5 shows a partial cross-sectional view through an example of a locating device included within the X-ray machine of FIG. 3.

FIG. 5 shows an example of a locating device 40 which may be connected to the patient table 20. The locating device 40 serves to accommodate or locate the patient's breast within the cutout portion 21. In the illustrated embodiment, a vacuum pump 42 is connected via tubing 41 for securing the patient's breast 31 within the locating device 40 by sub-atmospheric pressure.

As set forth above, an X-ray machine for imaging a female breast comprises a patient table 20 from which a gantry 10 of a spiral computer tomograph is rigidly and mechanically suspended. The patient table 20 has a breast cut-out portion 21 through which a breast 31 of a patient 30 is suspended downwards, preferably in the direction towards the gantry 10. The gantry 10 has a gantry lift drive 11 with which it can be moved relative to the patient's table. The gantry 10 rotates around the patient's breast to image the breast. A displacement of the gantry 10 along a longitudinal direction of the breast, e.g., in a vertical direction, is performed simultaneously with rotation and/or intermittently at regular intervals of time. In some embodiments, the vertical displacement can be performed continuously at constant speed, or proportionally to the rotational speed of the gantry. Alternatively, the vertical displacement may be performed stepwise, so that for example a vertical displacement of a distance equal to the width of the detector 14 is made following each revolution of the gantry.

The X-ray machine described herein makes it possible to perform X-ray exposures with high resolution. For example, a resolution of the X-ray machine described herein may be on the order of magnitude of about 10 micrometers to about 500 micrometers. In one embodiment, a resolution up to about 100 micrometers may be obtained with the X-ray machine described herein. At these resolutions, even the smallest mechanical tolerances and fluctuations can appreciably impair image quality.

In some X-ray machines, the gantry is put into a suitable exposure position before an exposure is made. After the gantry is stopped, periods ranging from several fractions of a second up to seconds are allowed to pass so that mechanical vibrations can decay before the next exposure is performed. However, the gantry described herein utilizes a spiral computer tomograph. Gantries of this sort cannot be stopped to minimize mechanical vibrations, since continuous rotation of the gantry around a breast occurs at the same time as an exposure. As a result, mechanical vibrations and tolerances directly affect image quality in gantries comprising spiral CTs.

A mechanically rigid connection between the gantry 10 and the patient table 20 is, therefore, of substantial importance to the X-ray machine described herein. A mechanically rigid connection is needed to minimize movement artefacts caused by mechanical vibrations and positional tolerances of the gantry with respect to a breast during high-resolution imaging. Accordingly, the gantry lift drive 11 also must be designed to be mechanically rigid. The mechanically rigid design of the X-ray machine described herein enables substantially higher quality images to be obtained than with systems, in which a patient's table and gantry are set up or suspended separately. Furthermore, mechanical tolerances or a possible bending of the patient table 20 do not affect the accuracy of the measurements obtained with the X-ray machine described herein. Thus, the resolution can be optimized, e.g., by arranging the central ray 52 of the beam 16 in a region close to a wall of a breast.

As shown in FIG. 4, the central ray 52 is the ray vertically incident on the detector 14. It is desired that the central ray 52 be as close as possible to the breast wall of the patient 30, in order to cover a region of the breast that is as large as possible. Thus, the X-ray tube 15 and the detector 14 are preferably disposed so that, the central ray 52 of the beam 16 is located on the side of the beam that faces the patient table 20. The best resolution is achieved with the central ray 52, thus, it is desired that the central ray 52 be disposed as close as possible to the patient table without penetrating the table. With the arrangement, it is possible to prevent vibrations and positional tolerances of the gantry and other components of the X-ray machine from impairing the high imaging quality of images achievable with the central ray.

In order to further improve accuracy of the X-ray machine, a locating device 40 is provided for a breast. Like the gantry, the locating device 40 may also be rigidly mechanically connected to the patient table 20. However, for reasons of hygiene, the locating device 40 can also be detachable from the table. In one embodiment, the locating device 40 operates by means of a vacuum that can be produced with a vacuum pump 42.

Another advantage resides in the extremely compact construction of the X-ray machine described herein. For example, a spiral computer tomography (CT) gantry consumes less space than other gantries, which require detectors of large surface area to image a whole breast. Due to the spiral recording, a substantially smaller detector can be used in the spiral CT gantry described herein. The use of a smaller detector also results in a substantially flatter gantry. In one embodiment, the height of the gantry 10 may be within a range of about 5 cm to about 20 cm. In one embodiment, the height of the gantry may be 10 cm. For this reason, and because of the rigid mechanical suspension of the gantry from the table, the space between the gantry 10 and a floor located below the gantry is freely accessible and can therefore be walked upon by a person performing the examination. Additional examination instruments, such as biopsy instruments, can also be disposed within this space. Because of the free accessibility of the space below the gantry, the performance of therapy with simultaneous recording of images is possible.

Furthermore, incorporating the gantry 10 with the patient table 20 enables exposures to be taken up to the lower edge of the patient table.

Another advantage of the X-ray machine described herein is that the patient table 20 comprises an adjustable height. For example, a patient table lift drive 22 coupled to patient table 20 may be used for lifting or adjusting the height of the patient table. As the gantry 10 is suspended from the patient table 20, the height of the patient table can be freely adjusted. With an adjustment of height, additional space can be created for additional examination instruments or even for an upright working position of a person performing the examination. The patient table 20 may be tiltable along axis 60 (FIG. 1), in some embodiments, providing additional workspace for the person performing the examination.

In some embodiments the X-ray machine is provided with wheels (23, FIG. 2), so that it can be moved for use at different sites. The wheels enable the machine to be used in other diagnostic facilities or with other instruments. For example, the moveable X-ray machine can be oriented with respect to another X-ray machine, an ultrasonic instrument, or a biopsy facility. As the gantry 10 is rigidly mechanically suspended from the table, an adjustment of the gantry with reference to the table is not altered by movement of the table. Thus, the image quality and also the precision of location remain constant.

The term "rigid mechanical connection" is hereby understood to be a connection which, although capable of being released, connects parts in a manner so that mechanical movements during operation are smaller than the resolution of the X-ray machine (which, in one embodiment, comprises a resolution on an order of magnitude of about 10 micrometers up to about 500 micrometers, or more preferably up to about 100 micrometers).

It will be appreciated to those skilled in the art having the benefit of this disclosure that this disclosure is believed to provide X-ray machines for imaging a breast. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. An X-ray machine for imaging a breast of a female patient, comprising:
   an approximately horizontally disposed patient table with a cut-out portion for accommodating a breast of a female patient;
   a gantry rigidly mechanically suspended from the patient table, wherein the gantry comprises an X-ray tube and an X-ray detector, and wherein the gantry is adapted to rotate about an approximately vertical rotational axis in a continuous rotational movement for imaging a breast, and wherein the gantry is further adapted to be moved in a vertical direction during said rotational movement.

2. The X-ray machine according to claim 1, wherein the X-ray tube and the X-ray detector are disposed so that a central ray of a beam of rays from the X-ray tube is located on a side of the beam nearest the patient table.

3. The X-ray machine according to claim 1, further comprising a locating device for locating the breast within the cut-out portion, wherein the locating device is rigidly mechanically suspended from the patient table.

4. The X-ray machine according to claim 1, further comprising a patient table lift drive coupled to the patient table for adjusting a height of the patient table.

5. The X-ray machine according to claim 1, wherein the patient table comprises wheels, which allow the patient table to be moved.

6. The X-ray machine according to claim 1, wherein the patient table is tiltable.

* * * * *